United States Patent [19]

Karger et al.

[11] Patent Number: 4,997,537
[45] Date of Patent: Mar. 5, 1991

[54] HIGH PERFORMANCE MICROCAPILLARY GEL ELECTROPHORESIS

[75] Inventors: Barry L. Karger, Newton; Aharon Cohen, Brookline, both of Mass.

[73] Assignee: Northeastern University, Boston, Mass.

[21] Appl. No.: 406,080

[22] Filed: Sep. 12, 1989

Related U.S. Application Data

[63] Continuation-in-part of Ser. No. 359,728, May 1, 1998, which is a continuation of Ser. No. 921,311, Oct. 21, 1986, Pat. No. 4,865,706, which is a continuation-in-part of Ser. No. 143,442, Jan. 12, 1988, Pat. No. 4,865,707.

[51] Int. Cl.[5] .................. G01N 27/26; G01N 27/28; B01D 57/02
[52] U.S. Cl. .............................. 204/182.8; 204/299 R
[58] Field of Search .............. 204/182.8, 180.1, 299 R

[56] References Cited

U.S. PATENT DOCUMENTS

| | | | |
|---|---|---|---|
| 2,748,074 | 5/1956 | Davis et al. | 204/299 |
| 3,616,457 | 10/1971 | Hjerten | 204/299 |
| 3,691,054 | 9/1972 | Cawley | 204/299 |
| 3,728,145 | 4/1973 | Hjerten | 117/54 |
| 3,783,118 | 1/1974 | Hjerten | 204/180 G |
| 3,876,775 | 4/1975 | Izaka et al. | 424/177 |
| 3,956,273 | 5/1976 | Guiseley | 260/209 R |
| 4,118,481 | 10/1978 | Schnabel et al. | 424/177 |
| 4,132,769 | 2/1979 | Osther | 424/1 |
| 4,139,346 | 2/1979 | Rabbani | 422/56 |
| 4,152,410 | 5/1979 | Ishii | 424/1 |
| 4,204,929 | 5/1980 | Bier | 204/180 R |
| 4,205,129 | 5/1979 | Podolsky et al. | 435/193 |
| 4,275,196 | 6/1981 | Shainoff | 536/115 |
| 4,284,491 | 8/1981 | Vesterberg | 204/299 R |
| 4,290,911 | 9/1981 | Cook et al. | 252/316 |
| 4,312,727 | 1/1982 | Shainoff | 204/180 G |
| 4,312,739 | 1/1982 | Hansson et al. | 204/299 R |
| 4,319,975 | 3/1982 | Cook | 204/180 G |
| 4,319,976 | 3/1982 | Gurske | 204/180 G |
| 4,321,121 | 3/1982 | Gurske | 204/180 G |
| 4,338,396 | 7/1982 | Kiyasu | 435/17 |

(List continued on next page.)

FOREIGN PATENT DOCUMENTS

| | | | |
|---|---|---|---|
| 0272925 | 6/1988 | European Pat. Off. | |
| 61-114115 | 5/1986 | Japan | 204/182.8 |
| 63-210766 | 9/1988 | Japan | 204/299 R |
| 63-210767 | 9/1988 | Japan | 204/299 R |
| 63-210768 | 9/1988 | Japan | 204/299 R |
| 1233907 | 6/1971 | United Kingdom | |

OTHER PUBLICATIONS

B. J. Radola, "Ultra-Thin—Layer-Isoelectric Focusing" Electrophoretic Techniques; Academic Press (London), pp. 101-104.

(List continued on next page.)

Primary Examiner—John F. Niebling
Assistant Examiner—John S. Starsiak, Jr.
Attorney, Agent, or Firm—Weingarten, Schurgin, Gagnebin & Hayes

[57] ABSTRACT

A microcapillary column for high performance electrophoresis. A preferred column includes a microcapillary, a thin layer of coating material covalently bonded to the inner surface of the microcapillary wall, a thin layer of a hydrophilic polymer absorbed on the layer of coating material, and a gel comprising polyacrylamide polymerized in the tube, filling it. The gel-containing microcapillary is prepared by covalently bonding a layer of a suitable coating material to the inner surface of the microcapillary wall, applying a layer of hydrophilic polymer, and then causing a mixture of monomer with or without crosslinking agent, initiator, and polymerization catalyst to react in the bore of the microcapillary to form a polymeric matrix. In electrophoresis, the gel-containing microcapillary provides peak efficiencies in excess of 100,000 theoretical plates and in some instances over 1,000,000 theoretical plates within separation times of less than thirty minutes, permits trace level determinations of molecular weights, and permits electrophoretic operation at fields of 300 V/cm or higher, resulting in extremely high resolution separations.

8 Claims, 3 Drawing Sheets

U.S. PATENT DOCUMENTS

| | | | |
|---|---|---|---|
| 4,358,358 | 11/1982 | Rhodes | 204/299 R |
| 4,362,612 | 12/1982 | Bier | 204/301 |
| 4,415,428 | 11/1983 | Nochumson et al. | 204/299 |
| 4,415,655 | 11/1983 | de Castro et al. | 435/17 |
| 4,427,658 | 1/1984 | Maubois et al. | 424/177 |
| 4,442,655 | 4/1984 | Stroetmann | 53/428 |
| 4,443,427 | 4/1984 | Reinherz et al. | 424/1.1 |
| 4,451,446 | 5/1984 | Vandevelde et al. | 424/92 |
| 4,460,694 | 7/1984 | Fletcher | 436/531 |
| 4,461,833 | 7/1984 | Gordon | 435/183 |
| 4,471,058 | 9/1984 | Smith et al. | 436/518 |
| 4,481,094 | 11/1984 | de Castro | 204/180 G |
| 4,503,147 | 3/1985 | Nakajima et al. | 435/25 |
| 4,512,896 | 4/1985 | Gershoni | 210/635 |
| 4,533,307 | 8/1985 | Ansorge | 204/299 R X |
| 4,548,869 | 10/1985 | Ogawa et al. | 428/474.7 |
| 4,548,870 | 11/1985 | Ogawa et al. | 428/474.7 |
| 4,579,783 | 4/1986 | Ogawa et al. | 428/475.2 |
| 4,582,868 | 4/1986 | Ogawa et al. | 524/211 |
| 4,588,492 | 5/1986 | Bier | 204/301 |
| 4,600,641 | 7/1986 | Ogawa et al. | 428/355 |
| 4,613,459 | 9/1986 | Cantor et al. | 530/351 |
| 4,640,759 | 2/1987 | Hashiue et al. | 204/299 R |
| 4,650,556 | 3/1987 | Hashiue et al. | 204/182.7 |
| 4,650,674 | 3/1987 | Aggarwal et al. | 424/85 |
| 4,657,656 | 4/1987 | Ogawa | 204/299 R |
| 4,665,164 | 5/1987 | Pernemalm et al. | 536/120 |
| 4,666,829 | 5/1987 | Glenner et al. | 435/6 |
| 4,668,359 | 5/1987 | Postle et al. | 204/182.7 |
| 4,680,201 | 7/1987 | Hjerten | 204/182.9 X |
| 4,690,749 | 9/1987 | Van Alstine et al. | 204/299 R X |
| 4,699,705 | 10/1987 | Ogawa et al. | 204/299 R |
| 4,725,343 | 2/1988 | Hjerten et al. | 204/183.2 |
| 4,747,919 | 5/1988 | Anderson | 204/182.8 |
| 4,865,706 | 9/1989 | Karger et al. | 204/182.8 |
| 4,865,707 | 9/1989 | Karger et al. | 204/182.8 |

OTHER PUBLICATIONS

Allen & Lack, "Standardization in Isoelectric Focusing" in *New Directions in Electrophoretic Methods*, (1987), pp. 117–119.

Chrambach & Bocek, *Trends in Anal. Chem.*, 4, 224 (1985).

Giddings, *Separation Science*, 4, 181–189 (1969).

Hjerten, *Chromatographic Reviews*, 9, 122–219 (1967).

Hjerten, *J. Chromatography*, 270, 1–6 (1983).

Hjerten, *J. Chromatography*, 347, 191–198 (1985).

Jorgenson, "Electrophoresis", *Anal. Chem.*, 58(7), (1986).

Jorgenson & Lukacs, *Anal. Chem.*, 53, 1298 (1981).

Jorgenson & Lukacs, *Clin. Chem.*, 27, 1553, (1981).

Jorgenson & Lukacs, *Science*, 222, 266–272, (1983).

Laemmli, *Nature*, 277, 680, (1970).

Lederer, M., *J. Chromatog.* 390, 468, (1987).

Postel et al., *J. Electrophoresis*, 6, 599, (1985).

Radola, in *Electrophoretic Techniques*, London: Acadamic Press, pp. 101–104.

Radola, "Rehydratable Polyacrylamide Gels" in *New Directions in Electrophoretic Methods*, 1987, pp. 68–69.

Tanaka, *Polymer*, 20, 1404, (1979).

Terabe, *Anal. Chem.*, 56, 111–113, (1984).

Verheggen & Van De Venne, *J. Chromatog.*, 123, 139 (1976).

Weber, *J. Biol. Chem.*, 244, 4406, (1969).

M. J. Gordon, X. Hung, S. L. Petaney, Jr., and R. N. Zare, *Science*, 242, 224, (1988).

B. L. Karger, A. S. Cohen and A. Guttman, *J. Chromatog.*, 492, 585, (1989).

Computer Printout from Search.

HIGH PERFORMANCE MICROCAPILLARY GEL ELECTROPHORESIS

CROSS-REFERENCE TO RELATED APPLICATIONS

This is a continuation-in-part of application Ser. No. 07/359,728, filed May 31, 1989, pending, which is hereby incorporated by reference. Application Ser. No. 07/359,728 is a continuation of parent application Ser. No. 06/921,311, filed October 21, 1986, now U.S. Pat. No. 4,865,706. A related application, is Ser. No. 07/143,442, filed Jan. 12, 1988, now U.S. Pat. No. 4,865,707 which is another continuation-in-part application based on the same parent application.

FIELD OF THE INVENTION

This invention relates to electrophoresis, and more particularly, to gel-containing microcapillary columns for high performance analytical electrophoresis.

BACKGROUND OF THE INVENTION

Electrophoresis is one of the most widely used separation techniques in the biologically-related sciences. Molecular species such as peptides, proteins, and oligonucleotides are separated by causing them to migrate in a buffer solution under the influence of an electric field. This buffer solution normally is used in conjunction with a low to moderate concentration of an appropriate gelling agent such as agarose or polyacrylamide to minimize the occurrence of convective mixing.

Two primary separating mechanisms exist, separations based on differences in the effective charge of the analytes, and separations based on molecular size. The first of these mechanisms is limited to low or moderate molecular weight materials in the case of separations of oligonucleotides because in the high molecular weight range the effective charges of these materials become rather similar, making it difficult or impossible to separate them. In the case of proteins, charge and size can be used independently to achieve separations. Separations based on molecular size are generally referred to as molecular sieving and are carried out employing as the separating medium gel matrices having controlled pore sizes. In such separating systems, if the effective charges of the analytes are the same, the separation results from differences in the abilities of the different sized molecular species to penetrate through the gel matrix. Smaller molecules move relatively more quickly than larger ones through a gel of a given pore size. Oligonucleotides and medium to high molecular weight polypeptides and proteins are commonly separated by molecular sieving electrophoresis. In the case of proteinaceous materials, however, it is first generally necessary to modify the materials to be separated so that they all have the same effective charges. This is commonly done by employing an SDS-PAGE derivatization procedure, such as is discussed in "Gel Electrophoresis of Proteins," B. D. Hames and D. Rickwood, Eds., published by IRL Press, Oxford and Washington, D.C., 1981. The contents of this book are hereby incorporated herein by reference.

Sometimes it is desirable to separate proteinaceous materials under conditions which pose a minimal risk of denaturation. In such cases system additives such as urea and SDS are avoided, and the resulting separations are based on differences in both the molecular sizes and charges.

Most electrophoretic separations are today conducted in slabs or open beds. However, such separations are hard to automate or quantitate. Extremely high resolution separations of materials having different effective charges have been achieved by open tubular free-zone electrophoresis and isotachophoresis in narrow capillary tubes. In addition, bulk flow can be driven by electroosmosis to yield very sharp peaks. Such high efficiency open tubular electrophoresis has not generally been applied to the separation of medium to high molecular weight oligonucleotides, however, since these materials have very similar effective charges, as indicated above. In addition, open tubular electrophoresis does not provide size selectivity for proteinaceous materials. The questions thus arise whether electrophoresis on gel-containing microcapillaries can be employed to achieve high resolution separations of oligonucleotides, and whether the conventional procedure of SDS-PAGE can be accomplished on such microcapillaries. As demonstrated by the present disclosure, the answers to these questions are affirmative, although given its potential importance as a separating technique in the biological sciences, surprisingly little attention has been paid to microcapillary gel electrophoresis.

Hjerten has published an article in the *Journal of Chromatography*. 270, 1-6 (1983), entitled "High Performance Electrophoresis: The Electrophoretic Counterpart of High Performance Liquid Chromatography," in which he employs a polyacrylamide gel in tubes having inside dimensions of 50-300 micrometers, and wall thicknesses of 100-200 micrometers. However, this work suffers from limited efficiency and relatively poor performance due in part to the use of relatively wide bore capillaries, relatively low applied fields, high electrical currents, and insufficient suppression of electroendosmosis. He has also obtained U.S. Pat. No. 3,728,145, in which he discloses a method for coating the inner wall of a large bore tube with a neutral hydrophilic substance such as methyl cellulose or polyacrylamide to reduce electroendosmosis in free-zone electrophoresis in open tubes. In a later patent, No. 4,680,201, Hjerten discloses a method for coating the inner wall of a narrow bore capillary with a monomolecular polymeric coating of polyacrylamide bonded to the capillary wall by means of a bifunctional reagent. These capillaries are also open tubes to be used for free-zone electrophoresis. In the background section of the '201 patent, it is stated that coating the inner wall of the electrophoresis tube with a polymeric substance to reduce adsorption and electroendosmosis suffers from the drawbacks that the coating material must be renewed periodically since it apparently flushes out of the capillary during use, and that relatively thick layers necessary for complete coating cause zone deformation in electrophoresis. This '201 patent thus teaches away from coating the wall of a capillary with a polymeric substance applied as an adsorbed layer, and discloses instead that for suppression of electroendosmosis a monomolecular layer of polyacrylamide should be covalently attached to the tube wall.

The small amount of work in the field of gel electrophoresis in capillaries by researchers other than the present applicants has generally resulted in columns which were not highly stable and could not be subjected to sufficiently high electric fields to achieve high efficiencies and high resolution separations. Improved gel filled capillary columns for electrophoresis which provide superior stability, efficiency, and resolution would be of great value in bioanalytical chemistry.

SUMMARY OF THE INVENTION

The above-identified need for stable and efficient gel-filled capillary electrophoresis columns is answered by the present invention, which provides an improved gel-containing microcapillary for high performance electrophoresis. It includes a microcapillary, a thin layer of coating material covalently bonded to the inner surface of the microcapillary wall, a thin layer of hydrophilic polymer adsorbed on the layer of coating material, and a polymeric gel filling the interior cavity of the microcapillary.

The layer of coating material between the microcapillary wall and the layer of hydrophilic polymer is generally a hydrophobic material and originates as a reagent possessing a reactive functional group capable of reacting with reactive functionalities on the interior surface of the capillary wall, silanol groups, for example. The remainder of the reagent may include a second reactive group which is capable in principle of reacting with vinyl monomers and optional crosslinking agents which when polymerized constitute the polymeric gel.

The layer of hydrophilic polymer effectively reduces electroendosmosis, stabilizes the column, and unexpectedly enables operation of the microcapillary column in high electric fields (or more exactly, high power), resulting in high resolution separations.

The improved gel-containing microcapillary of the invention is prepared as follows: first, the interior surface of a microcapillary is contacted with one or both of a basic and an acidic material to activate it, then it is treated with a solution of an appropriate coating reagent capable of covalent bonding to the microcapillary wall, resulting in formation of a layer of the coating material covalently attached to the inner surface of the microcapillary wall. Following this operation, the coated microcapillary is treated with a solution of a hydrophilic polymer, and this is dried, leaving a layer of hydrophilic polymer adsorbed on the layer of coating material. Next, the microcapillary is filled with a solution containing at least one monomer, and optionally at least one crosslinking agent, plus at least one free radical source and an appropriate catalyst, and this mixture is allowed to polymerize in the tube, ultimately forming a polymeric matrix which fills the capillary bore. As a final step, one end of the gel-containing microcapillary is cut off cleanly and squarely.

The gel-containing microcapillaries of the invention are unusually stable and function well under applied electric fields typically of 300 volts/cm or higher, and with currents typically up to approximately 50 microamperes or above. Under these conditions, extremely high resolution separations are obtained on very small amounts of material. In addition, the microcapillaries of the invention have been demonstrated to resolve mixtures of analytes as a linear function of the logarithms of their molecular weights. Accordingly, they permit convenient and accurate molecular weight determinations on nanogram or lower amounts of unknown biopolymers.

DESCRIPTION OF THE DRAWING

The invention will be better understood from a consideration of the following detailed description taken in conjunction with the drawing in which.

DETAILED DESCRIPTION OF THE INVENTION

Figure 1:
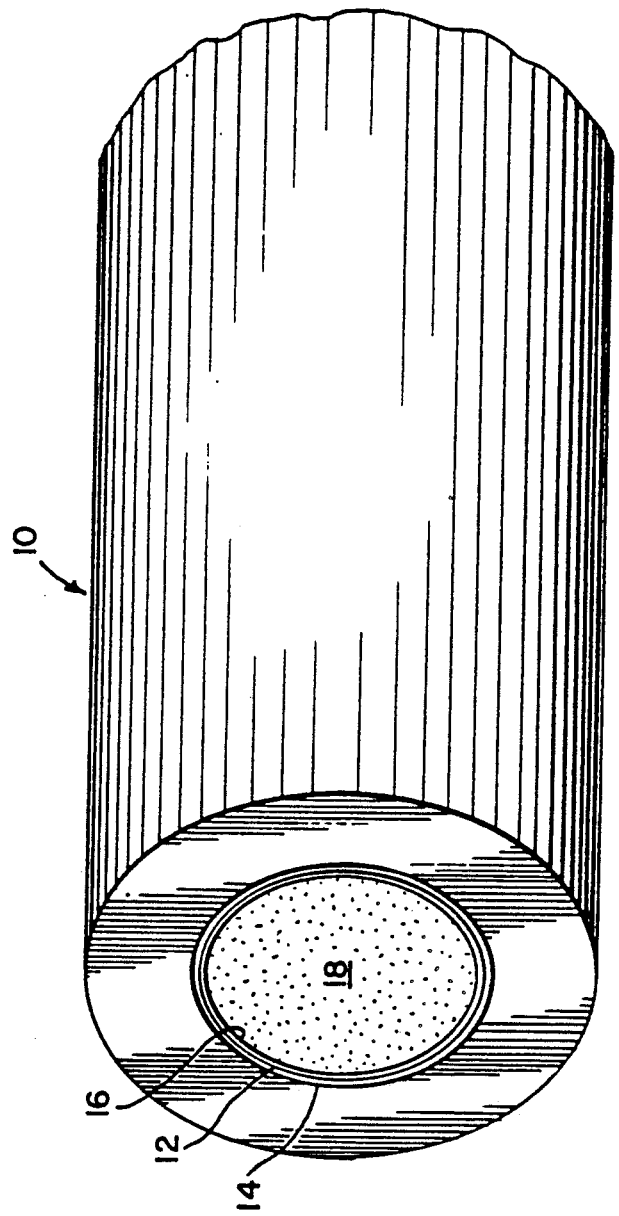
FIG. 1 shows a magnified perspective view of the end of the gel-containing microcapillary of the invention.

As shown in FIG. 1, the gel-containing microcapillary column of the invention includes a microcapillary 10, a layer 12 of coating material which is covalently bonded to the inner surface 14 of the microcapillary wall, a layer of hydrophilic polymer 16 adsorbed on layer 12, and a polymeric gel material 18 within the bore of this microcapillary.

The microcapillary may be made of any of a variety of materials provided that the detection system to be employed in the electrophoresis can function adequately with the particular material employed. Suitable materials include glass, alumina, beryllia, and TEFLON. Preferably, the microcapillary is made of fused silica.

The microcapillary dimensions are important because, for a given electric field, as the internal diameter of the microcapillary is reduced, the electric current and the resultant heating produced by a particular applied electric field is reduced. Thus, for highest resolution separations it is desirable that the microcapillary have a minimum internal diameter. With the improved hydrophilic polymer-containing microcapillaries of this invention, however, this factor is somewhat less important than formerly. Accordingly, microcapillaries having internal diameters in the range between 10 and 2000 micrometers function in the invention. A preferred range of internal diameters is 10 to 200 micrometers. A polyimide coating on the outer surface of the microcapillary permits easy handling of thin-walled microcapillaries.

The polymeric gel material 18 employed can be any polymer which has a pore structure which can be varied. It may or may not be crosslinked. Preferably, the polymeric gel is a crosslinked polymer whose pore structure is varied by varying the amounts of monomer and crosslinking agent, and the reaction conditions. Examples of suitable polymeric systems are polyacrylamide, agarose and mixtures of agarose and polyacrylamide. A preferred polymeric gel material is based on acrylamide and N,N' methylenebisacrylamide, the N,N'-methylenebisacrylamide serving as a crosslinking agent. Other possible crosslinking agents are N,N'(1,2-dihydroxyethylene)-bisacrylamide, N,N'-diallyltartardiamide, and N,N'-cystamine-bisacrylamide. Still other monomers and crosslinkers will suggest themselves to those skilled in the art.

The polymerization reaction is preferably initiated with ammonium persulfate or N,N,N',N'-tetramethyleneethylenediamine, though other free radical polymerization initiators may be employed, as known by those skilled in the art.

The layer 12 between the layer of hydrophilic polymer and the inner surface of the microcapillary wall is generally a hydrophobic material and is derived from a coating reagent which is capable of chemically bonding to the microcapillary wall. This reagent is generally a molecular chain having an appropriate reactive functional group at one end, though non-chain type molecules having appropriate functionalities will also serve. The end of the coating reagent which is to bond to the capillary wall carries a reactive functional group which can bond chemically to silanol groups or other reactive functionalities on the inner surface of the microcapillary. Such reactive functional groups of the reagent are typically reactive silanes such as trialkoxysilane, trichlorosilane, mono, di-, or tri-enolate silanes, and aminosilanes, where the silicon atom carries at least one group which may be readily displaced. Examples of suitable coating reagents are materials such as alkyl di- or tri- ethoxy or methoxy silanes, and alkylether di- or tri- ethoxy or methoxy silanes.

In a preferred embodiment, the coating reagent is a bifunctional material, which also contains a second functional group capable in principle of forming a covalent bond with the polymeric gel material. Such functional groups include vinyl, substituted vinyl, or any group which upon cleavage yields a free radical, but for practical purposes a vinyl group is preferred because it may then be possible to form the polymeric gel in the microcapillary and chemically bond it to the microcapillary wall simultaneously. Representative bifunctional reagents are 3-Methacryloxypropyl-trimethyoxysilane, and 3-Methacryloxypropyldimethylethoxysilane, shown as (a) and (b) below:

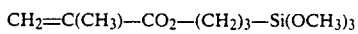

$CH_2=C(CH_3)-CO_2-(CH_2)_3-Si(OCH_3)_3$

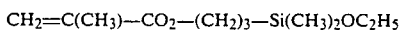

$CH_2=C(CH_3)-CO_2-(CH_2)_3-Si(CH_3)_2OC_2H_5$

Other possible bifunctional reagents are vinyltriacetoxysilane, vinyltri( -methoxyethoxy)silane, vinyltrichlorosilane, and methylvinyldichlorosilane, this list being intended as illustrative but not exhaustive.

In the case of capillaries to which the bifunctional reagents do not bond, e.g., TEFLON, the capillaries may be employed without a coating layer 12, provided that the hydrophilic polymer adsorbs to the microcapillary wall, or a layer of a polymer possessing the ability to adsorb to the microcapillary wall and to the hydrophilic layer may be employed.

The hydrophilic polymers which are useful in the invention include polyoxides such as polyoxymethylene; polyethers such as polyethylene oxide; polyalkylimines such as polyethyleneimine; polyamides such as polyacrylamide, polymethylacrylamide, poly-N,N-dimethylacrylamide, polyisopropylamide, and polyacrylylglycinamide; polyalkylene glycols such as polyethylene glycol and polypropylene glycol; and polymers of vinylic materials such as polyvinyl alcohol, polyvinyl acetate, and polyvinyl pyrrolidone. The molecular weight of the hydrophilic polymer is 600–500,000 Daltons or higher, preferably in the range of approximately 5000 to 200,000 Daltons. The hydrophilic polymers are preferably linear polymers. Polyethylene glycol is a preferred hydrophilic polymer.

For the improved microcapillary in which polyethylene glycol is employed as the hydrophilic polymer, the polyethylene glycol preferably has an average molecular weight of about 8000 Daltons or above, though material having an average molecular weight in the range 600 to 35,000 Daltons will serve. Polyethylene glycol having an average molecular weight of about 8000 Daltons or above is preferred, and is well-suited for use in the aqueous systems which are employed in this invention.

For highest resolution it is necessary that at least the front end of the gel-containing microcapillary be cleanly and squarely cut perpendicular to the central axis of the microcapillary. If the surface of the polymeric gel material which is exposed at the end of the microcapillary is uneven, it is impossible to make an injection of a uniform narrow band of sample, with the result that broad peaks are obtained.

The gel-containing microcapillaries of the invention are generally prepared as follows. First, the column is activated by heating it in excess of 100° C., generally for several hours, and then bringing its interior surface into contact with an acidic material such as a dilute solution of hydrochloric or nitric acid, and/or a basic material such as ammonia gas or a solution of a base. In the heating step a temperature of 110° to 200° C. may be conveniently employed. The time of such heating can vary from a few hours to overnight or longer. In one procedure, the activating step is accomplished by flushing the microcapillary with dry ammonia gas, generally for approximately 2 hours at a temperature of approximately 20–35° C., preferably at room temperature. In an alternative and preferred procedure, the column may be activated by heating it as above, then filling it with a solution of a base such as an alkali metal hydroxide, e.g., an 0.1 to 1N NaOH solution, leaving this solution in the microcapillary for at least approximately 1–3 hours and conveniently overnight at a temperature typically in the range 20–35° C., preferably at room temperature, then flushing with water.

The time and temperature employed in activating the microcapillary are selected such that they are sufficient to activate the microcapillary so that good bonding between the microcapillary and the bifunctional reagent is achieved.

The activated microcapillary is then flushed with at least 20 tubing volumes of a solution of the reagent to be employed in coating the tubing wall, and this is left to react for at least 1 hour and preferably 2 hours or longer at a temperature of 20–35° C., preferably at room temperature, filled with this solution of coating reagent. An alternative procedure is to place the filled microcapillary column in a vacuum oven overnight at about 60° C.

The solution of coating reagent is prepared in a nonaqueous solvent such as an alcohol, an ether, a ketone, or a moderately polar halogenated solvent and typically contains between 4 and 60% coating reagent by volume. Representative solvents are methanol, dioxane, acetone, and methylene chloride. After the coating reagent has been allowed to react with the inner wall of the microcapillary, excess unreacted reagent is optionally removed by rinsing the column with a suitable solvent such as methanol, followed by a further rinsing with water. Typically at least 100 tubing volumes of solvent and water are employed.

To form the layer of hydrophilic polymer, the coated microcapillary is filled with a degassed solution of hydrophilic polymer containing the buffer which will be employed for preparation of the gel filling to be described below. The concentration of the polymer in this solution is typically about 5-10% (w/v). The microcapillary is then held for several hours or overnight in a vacuum oven maintained at a temperature of about 125° C., until the tube is dry. This may be determined readily by inspecting the microcapillary under a microscope. The microcapillary is finally flushed with one or two tubing volumes of the buffer solution to remove excess crystals of the buffer material from the tube wall, while leaving the coating of hydrophilic polymer largely undisturbed.

For the case in which the hydrophilic polymer is polyethylene glycol, the polyethylene glycol is combined with degassed triply distilled water which has been cooled to about 10° C., then stirred while the temperature is raised slowly to room temperature. A clear transparent solution with no precipitate results. This solution is used to prepare the buffered solution of hydrophilic polymer discussed above.

Next, separate stock solutions of the monomers, any cross-linkers, the initiators, and free radical sources for the polymerization reaction are prepared, typically in 7 to 8 molar aqueous urea, though higher and lower concentrations of urea may be used. Gels which are intended to be non-denaturing are prepared without urea or other denaturing additives, and function well. The concentrations of these reagents are selected such that convenient aliquots of the solutions may be taken and mixed together to form a polymerization mixture having predetermined concentrations of monomer, cross-linker (if employed), and polymerization catalysts. Before mixing aliquots of these reagents together, the solutions are separately degassed for at least one hour. This degassing operation may be conducted in any of the several ways known to the art, but basically involves stirring the solutions mechanically or agitating them with ultrasound while simultaneously applying a low vacuum of approximately 20 to 30 millimeters of mercury. The preparation of these solutions is as known to the art, for example, as shown by Hames and Rickwood.

The total concentration of monomer and the concentration of crosslinking agent in these sorts of systems are generally expressed respectively as %T and %C, employing the terminology of Hjerten. In this regard, see Hjerten, Chromatographic Reviews, 9, 122-219 (1967). For the acrylamide N,N'-methylenebisacrylamide system preferably employed in this invention, the definitions of %T and %C are given below.

$$\% T = \frac{\text{grams of acrylamide + grams of bisacrylamide}}{100 \text{ milliliters of solvent}}$$

$$\% C = \frac{\text{grams of bisacrylamide} \times 100}{\text{grams of bisacrylamide + grams of acrylamide}}$$

The concentrations of monomer and any crosslinking agent are predetermined according to the porosity of the polymeric matrix desired. However, the concentrations of initiator and polymerization catalyst in the reaction mixture must be determined experimentally. This is done by preparing test solutions containing the desired %T and %C, but varying the amount of initiator and polymerization catalyst employed. In the event that SDS-PAGE electrophoresis is contemplated, sodium dodecylsulfate is also included in the reaction mixture in the requisite amount, typically 0.1%(w/v). These test solutions are allowed to polymerize at or below the temperature at which the electrophoresis is to be performed and the progress of the polymerization reaction is monitored by ultraviolet spectroscopy by observing the decrease in the absorbance of the vinyl double bond. Alternatively, the microcapillary may be observed visually. Levels of initiator and polymerization catalyst are selected which cause the polymerization to be essentially complete in a reasonable time, such as approximately 45 to 60 minutes.

Once the correct reagent concentrations have thus been determined, a fresh mixture of the polymerization reagents is prepared and injected into the microcapillary tube, taking care not to create bubbles. A small ID TEFLON tube is used to connect the microcapillary to the syringe employed to fill the microcapillary. When the microcapillary has been filled with polymerization mixture, the syringe is removed and both ends of the microcapillary are plugged by inserting them into septa, which are maintained while the polymerization reaction occurs.

The polymerization reaction is carried out at or below the temperature which is to be employed for subsequent electrophoresis on the microcapillary column. While the polymerization reaction is occurring, the reaction may be monitored separately in an aliquot of the reaction mixture by observing the loss of absorbance due to the vinyl groups by ultraviolet spectroscopy or visually. The polymerization reaction in the column and that in the separate monitor solution are the same, although the reaction in the capillary is much faster. When the test solution indicates the polymerization reaction is essentially over, which should be at a time between 45 and 60 minutes, the reaction is allowed to proceed for at least another two hours, preferably overnight, maintaining the temperature as indicated above.

An alternative and preferred polymerization procedure is to fill the microcapillary column with the solution of polymerization reagents as described above, then immediately place the column in a refrigerator at a temperature of 5-10° C. and allow the polymerization reaction to proceed overnight.

After the polymerization reaction in the microcapillary has gone essentially to completion, the caps are removed from the microcapillary ends and at least one end of the microcapillary is cut off cleanly and squarely. One way to accomplish this is to tightly sheath an end to be cut with small diameter TEFLON tubing, then cut the TEFLON-sheathed end cleanly and squarely perpendicular to the axis of the microcapillary using a microtome, which cuts through the TEFLON sheathing, the microcapillary material, and the polymeric gel, leaving a very smooth surface of gel material exposed at the end of the microcapillary. Alternatively and preferably, the capillary may be scored carefully at a right angle to its axis be means of a sapphire cleaver, and broken cleanly by bending it. The end of the microcapillary which has been thus cut is examined under a microscope to ascertain that the cutting operation in fact produced the requisite flatness of the exposed polymeric gel. If necessary, further cuts can be made until a suitably flat end is produced. Both ends of the microcapillary are generally treated in this fashion, although it is really only necessary to have a square cut end on the front of the microcapillary.

After its preparation, the column is placed in suitable electrophoresis apparatus and a low electric field of approximately 100 to 150 volts/cm is applied for a period of about one hour. If a very noisy baseline or a zero current condition is obtained, this indicates an improperly prepared column. In this event, a new microcapillary must be prepared.

In employing the gel-containing microcapillary column of the invention in electrophoresis, apparatus and techniques which are generally known to the those skilled in the art of open tube free zone microcapillary electrophoresis are employed. See, for example, B. L. Karger, A. S. Cohen, and A. Guttman, J. Chromatog. 492, 585 (1989); M. J. Gordon, X. Hung, S. L. Pentaney, Jr., and R. N. Zare, Science, 242, 224 (1988); and J. W. Jorgenson and K. D. Lukacs, Science, 222, 266–272 (1983). In capillary gel electrophoresis, resolution between two compounds is influenced by all the factors which affect band sharpness, including sample size, ionic materials in the samples, and the gel concentration. The latter factor is especially important, since if the gel concentration is too high the analytes are totally excluded from the column, while if it is too low little or no molecular sieving occurs. No single gel concentration is optimal for the resolution of all mixtures of proteinaceous materials or oligonucleotides. It is necessary to select appropriate gel concentrations for particular samples. Other important variables affecting electrophoresis in microcapillaries are the applied field and the electrical current employed. The sample is injected by the so-called "electrophoretic injection" technique, though other techniques known to the art, such as syringe layering injection, can serve. In the electrophoretic injection technique, the front end of the electrophoresis microcapillary is dipped into a sample solution containing an electrode of the appropriate polarity and an electric field of approximately 50 to 100 volts/cm is applied for a few seconds to cause electrophoresis of a small amount of the sample solution into the end of the microcapillary. The microcapillary is then transferred back to a solution of "running" buffer, the desired electrophoretic field is applied, and the electrophoresis is carried out in the normal way.

To aid in cooling and microcapillary, a cooling jacket or a related device is employed around the microcapillary over most of its length, excluding only the front and the rear ends of the microcapillary, which are respectively immersed in buffer solution and connected to the detector of the electrophoretic system. A cooling fluid is circulated through this jacket and maintained at whatever temperature is desired. Alternatively, an electrically controlled mechanical cooling device may be employed around the microcapillary column. Such "active" cooling is more effective in maintaining desired microcapillary temperatures than forced air or natural convection.

A method of performing high resolution molecular sieving electrophoresis for analytical purposes thus includes the steps of electrophoretically injecting an aliquot of a sample containing analytes to be separated into a gel-containing microcapillary column of the invention, applying an electric field of between 100 and 300 volts/cm or higher, allowing a current typically less than about 50 microamperes to pass through the microcapillary, and instrumentally detecting and measuring the separated analytes sequentially as they migrate past the detector.

The gel-containing microcapillaries of the invention separate analytes as a function of the logarithms of their molecular weights in a linear fashion. Accordingly, it is possible to determine molecular weights of unknown analytes by comparing their mobilities under standard electrophoretic conditions with a calibration chart plotting the log of the molecular weight of standard materials versus the mobilities of such standard materials.

A method of determining the molecular weight of an analyte therefore is to prepare a gel-containing microcapillary column according to this invention, select standard values of the electrophoretic operating parameters, the applied field being typically between 100 and 300 volts/cm or higher and the current being typically less than about 50 microamperes, injecting onto this microcapillary column an aliquot of a standard solution containing several standard analytes of known molecular weight, applying the selected standard values of the electrophoretic operating parameters to the microcapillary column to separate the standards, measuring mobilities of the known standards under the conditions of the electrophoresis, plotting the log of the molecular weight for each of the standard materials versus its mobility under the standard operating conditions, electrophoretically analyzing an unknown solution on the same column under the same conditions, measuring the mobilities of the analytes contained therein, and finally determining the molecular weights of these analytes from a comparison with the calibration plot.

The improved microcapillary columns containing a layer of hydrophilic polymer between the polymeric gel filling and the layer of wall coating material exhibit longer shelf lives and better stability in use than columns not containing such hydrophilic additives. Most importantly and unexpectedly, the improved microcapillary columns of the invention can be operated at high field strengths, which permit high resolution separations to be achieved in short analysis times.

The following experimental preparations are intended as exemplary only, and are not intended to limit or define the scope of the invention.

EXPERIMENTAL SECTION

Acrylamide, N,N'-methylenebisacrylamide, N,N,N',N'-tetramethyleneethylenediamine (TEMED), ammonium persulfate, sodium dodecylsulfate, TRIS buffer, and disodium hydrogen phosphate were all ultrapure or electrophoretic grade materials obtained from Swartz/Mann Biotech of Cleveland, Ohio. Somewhat less pure acrylamide from other sources could be suitably purified by recrystallizing three times and deionizing it by treatment with ion exchange resin. Urea was freshly obtained, and triply recrystallized from water/methanol. Proteins were obtained from the Sigma Chemical Company, St. Louis, Missouri and used as received. Water was triply distilled and deionized. Polyethylene glycol was obtained either from Aldrich or Sigma and was of analytical reagent grade. The fused silica microcapillary tubing preferably employed in the invention was obtained from Polymicro Technologies, Inc., Phoenix, Ariz. This company also supplies such tubing in various other dimensions. A sapphire cleaver useful in cutting off the ends of the microcapillaries was obtained from Ealing Electronics Corp., 22 Pleasant Street, South Natick, Mass. 01760.

Narrow bore TEFLON tubing (0.2–0.25 millimeters ID) was used for filling microcapillary tubes. All solutions were filtered through a nylon 66 or methylcellulose filter membrane having a 0.2 micrometer pore size. Analytical samples were kept frozen at −20° C. prior to use, and aliquots of these samples for experimental work were stored at 4° C. Proteins for SDS-PAGE work were prepared as known to the art.

A Soma S-3207 detector by Instrumentation for Research and Development, Inc., Kingston, Mass., was employed, and was modified for microcapillary work as described in the article by S. Terabe, et al, *Anal. Chem.*, 56, 111–113 (1984). Data were converted to digital form using a Nelson Analytical A/D Interface model 762 SA, and stored using an IBM PC/XT computer. Other equipment known to the art will also serve.

Preparation and Testing of Gel-Containing Microcapillary Having 7.5% T, 3.3% C, 0.1% SDS, and a Layer of Polyethylene Glycol Surrounding the Gel Fused silica microcapillary tubing having an ID of 75 micrometers, a wall thickness of about 150 micrometers, and a polyimide coating was employed. A 40 to 45 cm length of this tubing was taken for preparation of the gel-containing microcapillary. The polyimide coating was removed from a 2 cm section of one end of the tubing by burning. This end was ultimately connected to the detector of the electrophoresis apparatus.

The microcapillary tubing was heated overnight at about 120° C. in air, then filled with 1 M KOH solution and left overnight at room temperature. Next, the microcapillary was rinsed with about twenty column volumes of a 50% solution of 3-Methacryloxypropyltrimethyoxysilane in HPLC grade methanol at room temperature. The microcapillary, filled with bifunctional reagent solution, was then placed in a vacuum oven maintained at a temperature of 125° C. and a vacuum of approximately 2 mm of mercury and left overnight.

The coated microcapillary was next carefully filled with a previously degassed solution containing 6% w/v polyethylene glycol having a nominal molecular weight of about 35,000 Daltons, 0.1 M Tris borate buffer (pH=8), and 7 M urea, and then left overnight in a vacuum oven at a temperature of about 125° C. and a vacuum of about 2 mm of mercury, after which the microcapillary was found to be dry by microscopic examination. The treated microcapillary was flushed with about 1–2 tube volumes of buffer solution (below) and then cut to a length of somewhat greater than 20 cm from the window.

Buffer solution was prepared by dissolving 1.1 g of TRIS buffer in 100 ml of 7 molar urea solution, adding 0.01 g of EDTA and 0.1 g of sodium dodecyl sulfate, and adjusting the pH to 8 by the addition of boric acid.

A solution of acrylamide and N,N'-methylenebisacrylamide was prepared by combining 29 g of acrylamide and 1 g of N,N'-methylenebisacrylamide in 100 ml of buffer solution, giving a solution having a %T of 30% and a %C of 3.3%.

A solution of ammonium persulfate was prepared by dissolving 0.2 g of ammonium persulfate in 2 ml of the buffer solution.

The solutions of buffer, monomers, and ammonium persulfate were separately filtered through 0.2 micrometer filters and degassed for 2 hours by applying a vacuum of 20–30 mm of mercury.

0.75 g of the acrylamide-bisacrylamide solution was added to 10 ml of buffer solution, giving a final solution having %T=7.5% and %C=3.3%. This solution was filtered through a 0.2 μm filter and degassed under vacuum overnight at a vacuum of about 20–22 mm of water.

To a 0.5 ml aliquot of the acrylamide-bisacrylamide solution were added 7.5μl of a 5% v/v solution of electrophoresis grade TEMED and 7.5 μl of 5% w/v ammonium persulfate solution, and in excess of 50 μl of this polymerization mixture was forced through the microcapillary until no bubbles were observed exiting the microcapillary. The injection syringe was carefully removed from the TEFLON tubing while continuing the injection, to prevent introduction of bubbles into the microcapillary. Finally, both ends of the microcapillary were plugged with septa and the column was placed in a refrigerator and maintained between 5 and 10° C. overnight, during which time the polymerization occurred. Finally, the front end of the microcapillary was cut off in a microtome at a microcapillary migration distance (front end to detector) of 20 cm. The final gel-containing microcapillary was evaluated for one hour under an applied field of 100 volts/cm, and found to be satisfactory.

Figure 2:
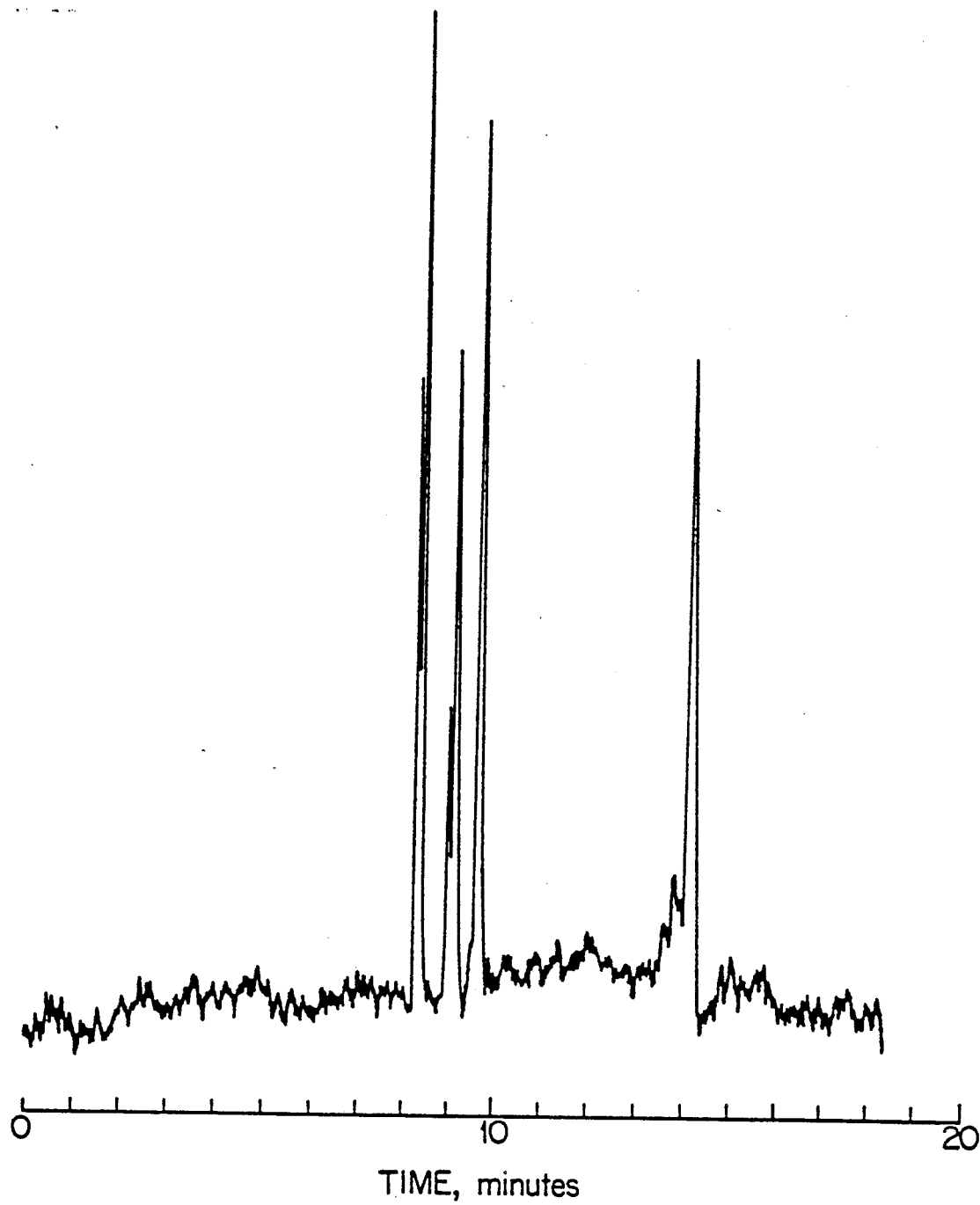
FIG. 2 shows an SDS-PAGE separation of four standard proteins, cytochrome C, lysozyme, myoglobin, and trypsinogen, on a microcapillary column of the invention containing 7.5% total monomer, 3.3% crosslinker, and 0.1% (w/v) of SDS. The pH of the buffer was 8.6, and electrophoresis was conducted under an applied field of 300 volts/cm and a current of 12-15 microamperes, over a 20 centimeter migration distance.

A mixture of four proteins, cytochrome C, lysozyme, myoglobin, and trypsinogen, was prepared for SDS-PAGE electrophoresis in the standard manner known to the art, then a sample of this solution was electrophoretically injected onto the microcapillary column by application of an electrical field of 100 volts/cm for 15 seconds. Electrophoresis was conducted at 300 volts/cm and a current of 15–17 μA over the 20 cm migration distance. Results are shown in FIG. 2.

Figure 3:
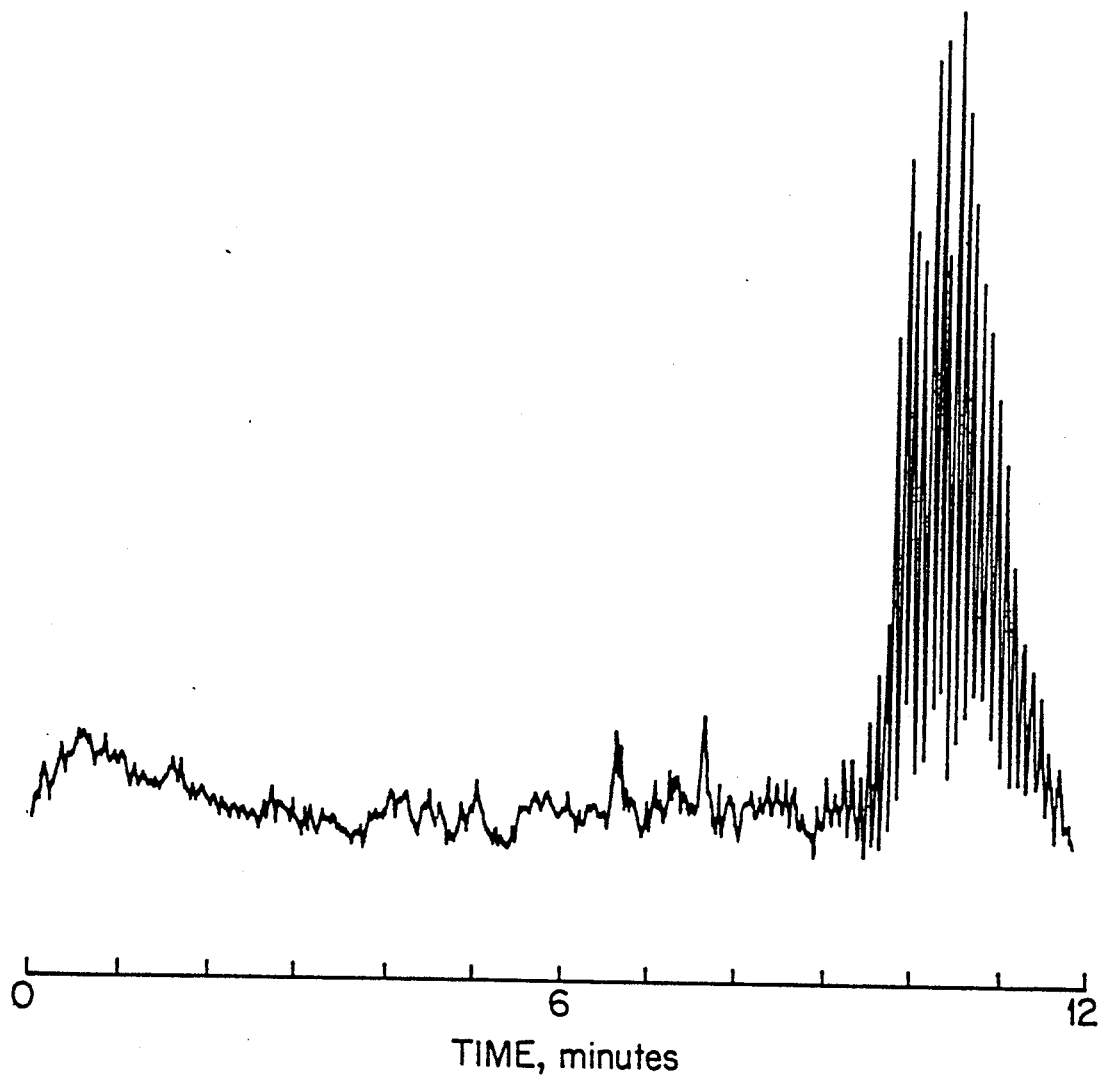
FIG. 3 shows an electrophoretic separation of poly(-deoxyadenylic acid) oligomers on a microcapillary column like that described with reference to FIG. 2, but without SDS, under the same electrophoretic conditions as were employed in the separation shown in FIG. 2.

Preparation and Testing of Gel-Containing Microcapillary Having 7.5%T, 3.3%C and a Layer of Polyethylene Glycol Surrounding the Gel A second microcapillary was prepared as above but without the inclusion of SDS. A mixture of poly(deoxyadenylic acid) was injected and separated by electrophoresis at 300V/cm with a current of 12–14 μA. Results are shown in FIG. 3.

Quality Control Testing of Microcapillary Columns

During their lifetimes, the gel-filled microcapillaries should be tested periodically for stability and reproducability by measuring the electrophoretic current at various applied fields. Well-made columns in good condition exhibit a constant resistance over a range of applied fields and this is repeatable over time. In this test the applied field (V/cm) is plotted against the measured current. A straight line with a constant slope (resistance) over time indicates the column is good. Typical experimental data for an SDS-gel capillary column are presented in Table I below.

TABLE I

| E (V/cm) | I (μA) |
|---|---|
| 100 | 6 |
| 200 | 12 |
| 300 | 18 |
| 400 | 22 |
| 500 | 28 |
| 600 | 33 |
| 700 | 40 |

These data are indicative of a well-made column, and also demonstrate the column can be operated under an applied electric field of 700 V/cm.

Other embodiments of the invention will be apparent to those skilled in the art from a consideration of this specification or practice of the invention as disclosed herein. It is intended that the specification and examples be considered as exemplary only, with the true scope and spirit of the invention being indicated by the following claims.

What is claimed is:

1. A gel-containing microcapillary column high precision and high performance electrophoresis, comprising:
    a microcapillary having an interior and a wall with an inner surface;
    a layer of coating material covalently bonded to said inner surface of said wall;
    a layer of hydrophilic polymer adsorbed on said layer of coating material; and
    a polymeric gel filling said interior cavity.

2. The microcapillary of claim 1 wherein said microcapillary is made of fused silica.

3. The microcapillary of claim 1 wherein said hydrophilic polymer is polyethylene glycol.

4. The microcapillary of claim 1 wherein polymeric gel further comprises a copolymer of acrylamide and at least one crosslinking agent.

5. The microcapillary of claim 1 wherein said coating material originates as a bifunctional reagent selected from the group consisting of 3-Methacryloxypropyl-trimethyoxysilane, 3-Methacryloxypropyldimethylethoxysilane, vinyltriacetoxysilane, vinyltri(-methoxyethoxy)silane, vinyltrichlorosilane, and methylvinyldichlorosilane.

6. A gel-containing microcapillary column for high precision high performance electrophoresis, comprising:
    a silica microcapillary having an interior cavity, a wall having an inner surface, and an internal diameter between 10 and 200 micrometers;
    a layer of coating material covalently bonded to said inner surface of said wall, said coating material being derived from 3-Methacryloxypropyl-trimethoxysilane or 3-Methacryloxypropyldimethylethoxysilane;
    a layer of polyethylene glycol adsorbed on said layer of coating material; and
    a gel comprising polyacrylamide filling said interior cavity.

7. The microcapillary of claim 6 wherein said gel is a copolymer of acrylamide monomer and N,N'-methylenebisacrylamide crosslinking agent.

8. A method of performing high resolution molecular sieving electrophoresis, comprising:
    injecting an aliquot of a sample containing analytes to be separated onto a gel-containing microcapillary column comprising:
    a microcapillary having an interior cavity and a wall with an inner surface;
    a layer of coating material covalently bonded to said inner surface of said wall;
    a layer of hydrophilic polymer on said layer of coating material; and
    a polymeric gel filling said interior cavity;
    applying an electric field of at least 100 volts/cm; and
    instrumentally detecting and measuring the separated analytes sequentially.

* * * * *

UNITED STATES PATENT AND TRADEMARK OFFICE
CERTIFICATE OF CORRECTION

PATENT NO. : 4,997,537         Page 1 of 2

DATED : March 5, 1991

INVENTOR(S) : Barry L. Karger, Aharon Cohen

It is certified that error appears in the above-identified patent and that said Letters Patent is hereby corrected as shown below:

Column 3, line 2, "gel filled capillary columns for" should read --gel-filled capillary columns for--;

Column 4, line 65, "N,N' methylenebisacrylamide, the" should read --N,N'-methylenebisacrylamide, the--;

Column 4, line 67, "agents are N,N'(1,2-" should read --agents are N,N'-(1,2- --;

Column 7, line 52, "Reviews, 9, 122-219 (1967)." should read --Reviews, $\underline{9}$, 122-219 (1967).--;

Column 9, line 14, "art of open tube free zone microcapillary" should read --art of open tube free-zone microcapillary--;

Column 9, line 17, "492, 585 (1989);" should read --$\underline{492}$, 585 (1989);--;

Column 9, line 47, "To aid in cooling and microcapillary" should read --To aid in cooling the microcapillary--;

Column 11, lines 13-14, "Anal. Chem., 56, 111-113" should read --Anal. Chem., $\underline{56}$, 111-113--;

UNITED STATES PATENT AND TRADEMARK OFFICE
CERTIFICATE OF CORRECTION

PATENT NO. : 4,997,537

DATED : March 5, 1991

INVENTOR(S) : Barry L. Karger, Aharon Cohen

It is certified that error appears in the above-identified patent and that said Letters Patent is hereby corrected as shown below:

Column 13, line 13, "microcapillary column high" should read --microcapillary column for high--;

Column 13, line 16, "having an interior and a wall" should read --having an interior cavity and a wall--.

Signed and Sealed this

Twenty-third Day of March, 1993

Attest:

STEPHEN G. KUNIN

*Attesting Officer*        *Acting Commissioner of Patents and Trademarks*